United States Patent [19]

Furnish

[11] Patent Number: 5,498,256
[45] Date of Patent: Mar. 12, 1996

[54] SURGICAL INSTRUMENT HANDLE

[75] Inventor: Greg Furnish, Lawrenceville, Ga.

[73] Assignee: Snowden-Pencer, Inc., Tucker, Ga.

[21] Appl. No.: 69,715

[22] Filed: May 28, 1993

[51] Int. Cl.⁶ .................................................. A61B 17/00
[52] U.S. Cl. ........................... 606/1; 606/170; 606/206; 606/208
[58] Field of Search .................... 606/170, 174, 606/205, 206, 208, 148, 142, 83, 1, 51, 52; 128/751

[56] References Cited

U.S. PATENT DOCUMENTS

| | | |
|---|---|---|
| 4,590,936 | 5/1986 | Straub et al. . |
| 4,644,651 | 2/1987 | Jacobsen ............................. 128/751 X |
| 4,950,273 | 8/1990 | Briggs ..................................... 606/113 |

FOREIGN PATENT DOCUMENTS 8103122  11/1981  WIPO .

OTHER PUBLICATIONS

Promotional Literature (catalog) Medicon Instrumente, (Date unkown).
Photocopy of actual Ethicon (MIC 608) instrument handle (Date unknown).
Promotional Literature, Snowden—Pencer (1990).
Excerpt from article on Laproscopic Suturing system, Karl Storz, Endoscopy–American, Inc. (Date unknown).
Promotional Literature, Jarit, Inc., Mar. (1992).
Promotional Literature, Aslan Medical Technologies (Date unknown).
Promotional Literature, Karl Storz GmbH & Co. (1991).
Promotional Literature, B. Braun–Dexon GmbH (Date unknown).
Promotional Literature, Access Surgical International, Inc. (Sep. 1992).
Promotional Literature, Endotec Endoscopic Technologies, Inc. (1993).

*Primary Examiner*—Michael H. Thaler
*Attorney, Agent, or Firm*—Needle & Rosenberg

[57] ABSTRACT

The present invention provides a hand-held surgical instrument with an improved handle, the instrument being of the type generally comprised of a handle and a tool with a body member having at least one articulated member thereon. The handle of the present invention has an elongated base, an elongated lever, means for connecting the lever and base at a rearward pivot point, means for actuating the surgical tool, utilizing movement of the handle lever between an open and a closed position, means for biasing the lever in an open position, and a means for securing the lever at a plurality of preselected points between the open and closed positions.

14 Claims, 3 Drawing Sheets

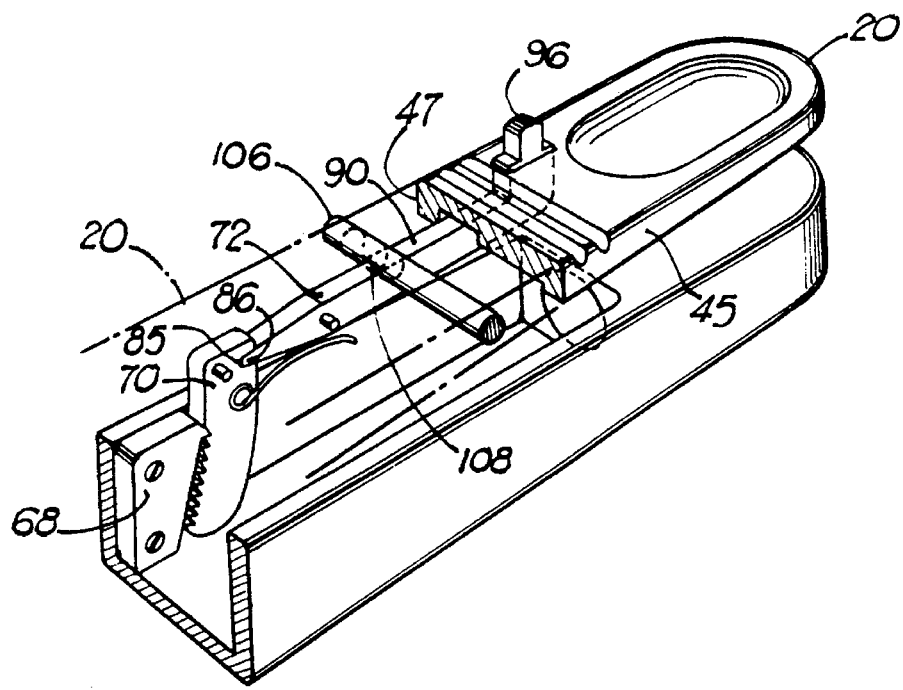
FIG 6
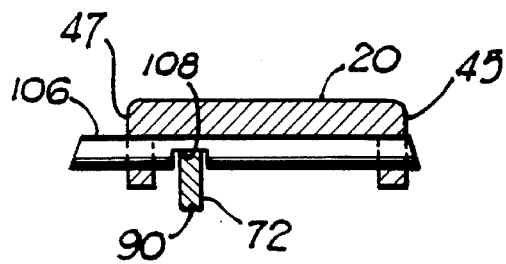 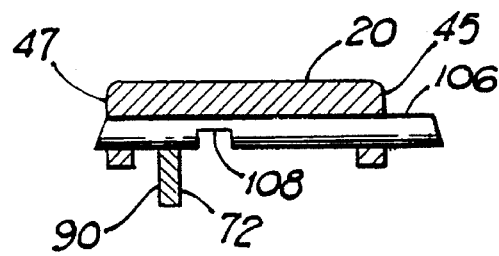
FIG 7A　　　FIG 7B

SURGICAL INSTRUMENT HANDLE

BACKGROUND OF THE INVENTION

1. Field of the Invention

This invention relates to handles for surgical instruments. In particular, this invention relates to an improved handle for hand held surgical instruments of the type having a tool with at least one articulated member thereon wherein the handle has a means for actuating the articulated member.

2. Background Art

Surgery is a learned art requiring many hours of advanced training and skills development that extends far beyond a thorough understanding of the medical principals involved, e.g., anatomy, physiology, principals of wound healing, and the like. The surgeon must also develop hand to eye coordination and acquire skills in the art of atraumatic tissue manipulation utilizing a variety of highly specialized surgical instruments.

The surgical instrument actually becomes an "extension" of the surgeon's hand. The surgeon must develop an ability to "feel" and respond, often delicately yet firmly, through his surgical instruments. Accordingly, there exists a need for instrument handles which are sensitive, responsive and ergonomically designed to augment the natural motions of the human hand.

The apposition between thumb and the index finger is the most sensitive and most often used means for delicate touching or for picking up small objects in every day affairs. Prior to the present invention, however, there were no surgical instrument handles designed to fully utilize the sensitive and delicate opposition capabilities of the thumb and index finger for movement of the lever arm of an instrument handle.

The actuating mechanism for handles of currently available surgical instruments are usually configured such that the pivot point is located between the handle lever and the articulated member (a forwardly located pivot point). The handle can have either one or two lever arms which are moveable about the pivot point. Such configuration is opposite to the natural pivot points of the hand.

One example of prior art handles of the type described above is the conventional "scissors" type handle with a forward pivot point, e.g., Mayo or Metzenbaum scissors, or Debakey forceps. The scissors handle design usually lacks a means for biasing the instrument tool in an open position. Of necessity, therefore, these scissors type handles have finger and thumb rings located at the free ends of the lever arms which provide a means for receiving force and balancing the instrument when both opening and closing the lever arms of the handle.

The scissors type handles are usually held by inserting the thumb through the thumb ring, balancing the scissors against the index finger and inserting one or more of the remaining digits into the finger ring of the opposite lever. Movement of the lever arms is accomplished by apposing the thumb and digits which are in the finger ring. This design requires increased muscular effort to open and close the levers and therefore fatigues the hand of the surgeon.

A second example of the forward pivot point configuration is the "pliers" type handle which is functionally similar to the scissors handle but without finger rings. In this configuration, movement of the levers from the open to the closed position is accomplished by closing the palm of the hand in a squeezing motion. A bow spring or other spring configuration located between the lever arms is sometimes included as a means to bias the handle in an open position to compensate for the lack of finger rings.

Neither the scissors nor the pliers type handles are capable of being held and moved by the tips of the fingers which results in a significant loss in sensitivity.

A third type of handle utilizes an actuator having two bowed springs connecting a rearwardly projecting actuator rod to handle levers which pivot about a forward pivot point. Although this handle may be held in a manner which allows for fingertip control, the forwardly located pivot point, opposite from the natural pivot point of the hand, results in loss of leverage and decreased sensitivity of the instrument. For fingertip control, the surgeon must sacrifice leverage by placing the fingertips away from the lever ends and closer to the forward pivot point.

One type of instrument which utilizes a rearwardly located pivot point is the forcep e.g., Adison, Potts-Smith, or general tissue forceps. Forceps utilize the thumb and index finger in a "pencil" grip fashion. However, forceps are not designed to activate an articulated member of a tool e.g., a needle holder, retractor, or hemostat. Rather the distal ends of the forcep lever arms actually comprise the tool itself.

The present invention satisfies the need in the art for a more sensitive and ergonomic handle by providing an instrument handle which is designed to functionally mimic and create functional harmony with the natural gripping mechanism and motion which exists between the thumb and index finger of the human hand.

SUMMARY OF THE INVENTION

The present invention provides a surgical instrument with an improved instrument handle with a base and lever with an activating arm which is connected to the base at a rearwardly located pivot point. The instrument is designed to be held in a "pencil grip" or "Vardon golf grip" position; both of which are natural gripping relationships between the index finger and opposable thumb.

The rearwardly located pivot point of the handle design of the invention functionally resembles the natural pivot points of the metacarpo-phalangeal joint of the index finger when the handle is held in the pencil grip fashion or of the carpo-metacarpal joint of the thumb when held in the golf grip manner. The handle of the present invention operates with fingertip control from the ends of the lever which increases leverage and sensitivity. The ergonomic design permits the surgeon to transfer force in a direct linear relationship from the hand to the articulated member of the surgical tool with precision, ease and delicacy.

The means for connecting the lever arm and base of the present invention may be an interchangeable leaf spring which also functions as the means for biasing the lever in an open position. This feature allows the resistance and sensitivity of the lever to be varied by changing the thickness and resistance of the spring.

Moreover, the rachet mechanism embodied by the present invention may be located within the body portion of the handle base, away from contact with the surgeon's gloves. This improved design prevents contamination of the surgical field resulting from the surgeon catching and tearing a glove in the rachet, which is often a problem with the rachet mechanisms of scissors type handles.

BRIEF DESCRIPTION OF THE DRAWINGS

FIG. 6 is a perspective view of a fragmentary portion of an alternate embodiment of the rachet locking mechanism with the rachet lever in the rest position.

FIG. 7A is a transverse cross-sectional view of the embodiment of FIG. 6, with the rachet lever locked in the rest position.

FIG. 7B is a transverse cross-sectional view of the embodiment of FIG. 6, with the rachet lever locked in the operable position.

DETAILED DESCRIPTION OF THE INVENTION

The present invention may be understood more readily by reference to the following detailed description of specific embodiments and the Figures included herein.

As used in the claims, "a" means one or more.

Figure 1:
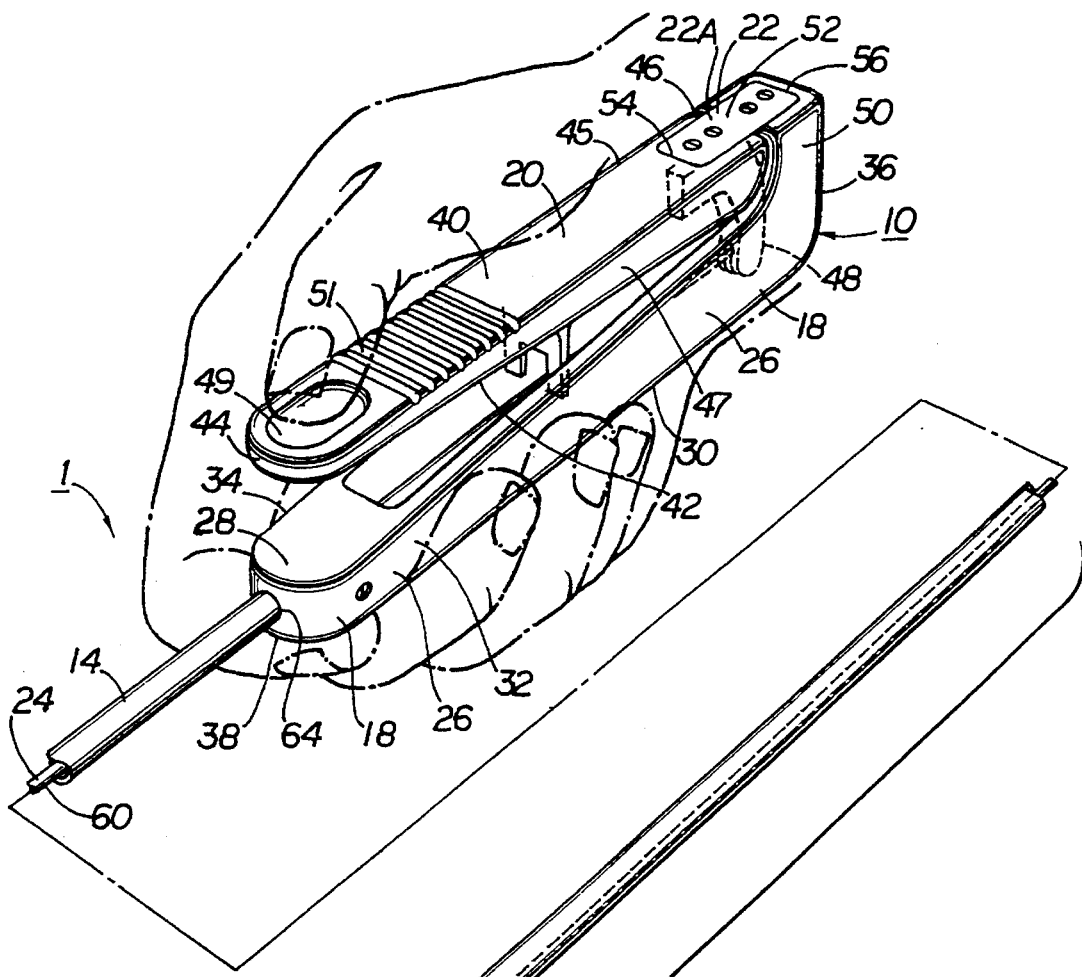
FIG. 1 is a segmented prospective view of one embodiment of the present invention.
Figure 2:
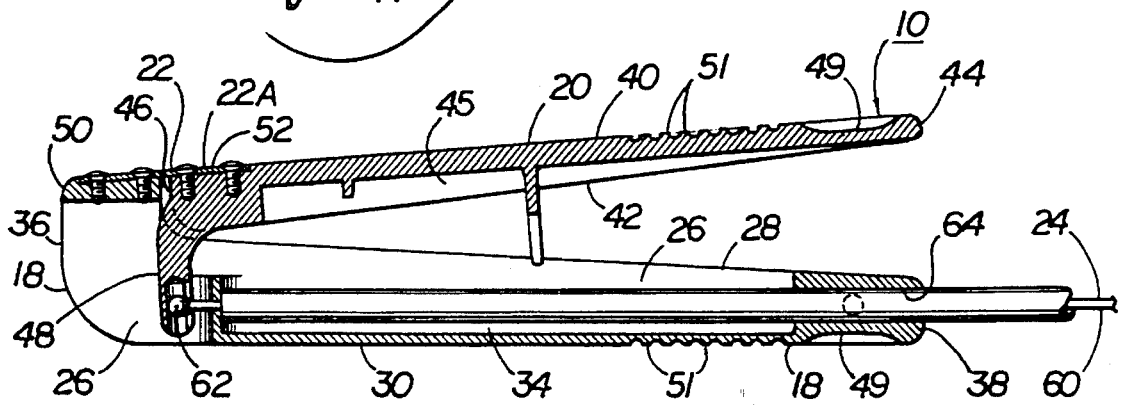
FIG. 2 is a longitudinal cross-sectional view of one embodiment showing the surgical instrument handle.

Referring now to FIG. 1 and FIG. 2, the present invention provides a hand-held surgical instrument 1 comprising a handle 10 and a tool 12 with a body member 14 having at least one articulated member 16 thereon, the handle 10 comprising: an elongated base 18; an elongated lever 20; a connecting means 22 for connecting the lever 20 to the base 18; a biasing means 22a for normally biasing the lever 20 in an open position; and an actuating means 24 for actuating the articulated member 16 of the tool 12. The elongated base 18 has a body portion 26, a top surface 28, an opposite bottom surface 30, a first side 32 and an opposite second side 34, a proximal end 36 and a distal end 38. The elongated lever 20 has a first surface. 40, an opposite second surface 42, a front end 44, a rear end 46, a first side 45, a second side 47 and an actuator arm 48 downwardly projecting from the rear end 46. As shown in FIG 1 and FIG. 2, the handle 10 may have fingertip depressions 49 and one or more grip ridges 51.

Figure 3:
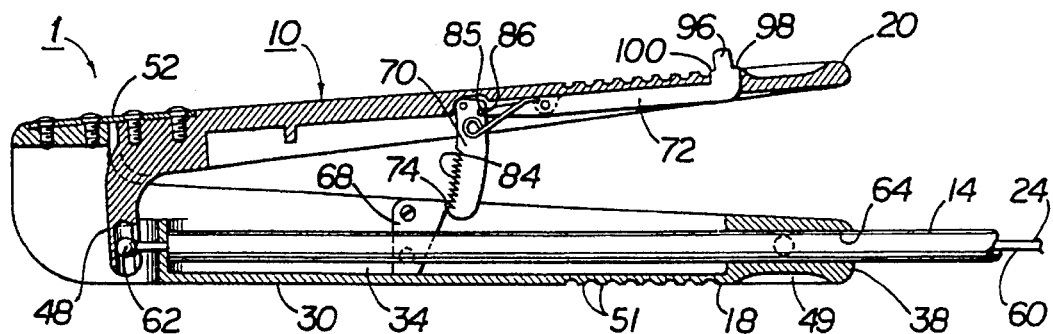
FIG. 3 is a longitudinal cross-sectional view of an alternate embodiment of the of the present invention showing the lever arm in an open position with the rachet engaged.
Figure 4:
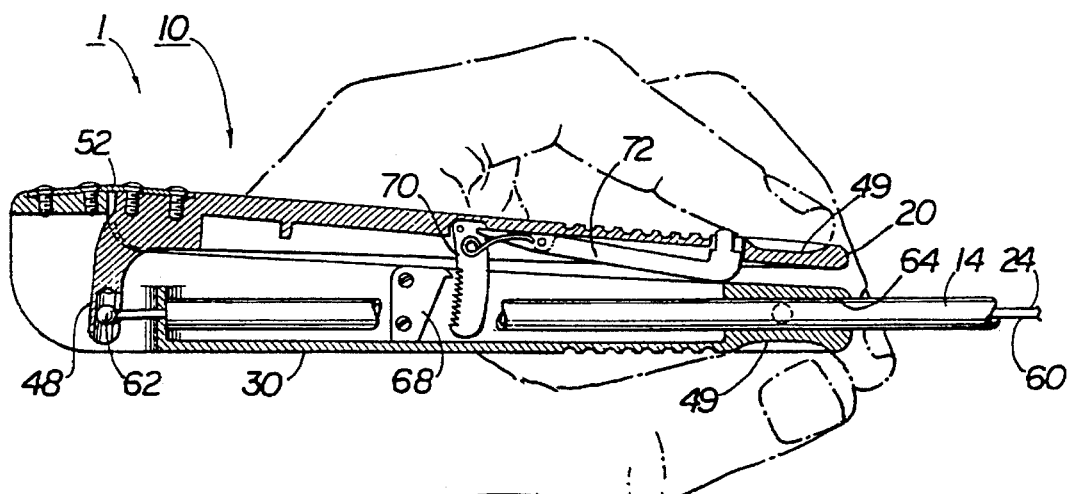
FIG. 4 is a longitudinal cross-sectional view one embodiment of the instrument in FIG. 3 showing the lever arm in the closed position with the rachet disengaged.

The connecting means 22 for connecting the rear end 46 of the lever 20 to the proximal end 36 of ate base 18 allows the lever 20 to pivot about a horizontal axis between an open position (shown in FIG. 3) and a dosed position (shown in FIG. 4). The base 18 and the lever 20 are juxtaposed to each other along their length, with the lever 20 extending forward from the connecting means 22 toward the distal end 38 of the base 18. The second surface 42 of the lever 20 is adjacent to the top surface 28 of the body portion 26 and the actuator arm 48 of the lever 20 projects into the body portion 26 of the base 18 adjacent the proximal end 36 of the base 18.

The actuating means 24 for actuating the articulated member 16 of the tool 12 is connected to the actuating arm 48 of the lever 20 such that movement of the lever 20 from an open position to a closed position causes movement of the articulated member 16.

As shown in FIGS. 1–4, the base 18 of the instrument 1 may comprise an arm 50 upwardly projecting from the proximal end 36, wherein the connecting means 22 connects the lever 20 to the arm 50. The connecting means 22 of the instrument 1 may comprise a leaf spring 52 having a preselected thickness with a first end 54 and an opposite second end 56. The first end 54 of the spring 52 is connected to the first surface 40 of the lever 20 adjacent the proximal end 46 of the lever and the second end 56 of the spring 52 is connected to the upwardly projecting arm 50 of the base.

In the embodiments depicted in the Figures, the leaf spring 52 may also function as the biasing means 22a of the instrument 1. The leaf spring 52 may be removably connected to the lever 20 and the base 18 such that the leaf spring 52 may interchangeably the comprised of one of a plurality of leaf springs of different preselected thicknesses thereby varying the resistance of the biasing means 22a. The leaf spring 52 may be removably attached to the lever 20 and the base 18 by means of machine screws 58.

The actuating means 21 of the instrument 1 may comprise an actuator rod 60 having a first end 62 and a second end (not shown), the second end of the rod 60 being connected to the articulated member 16 of the tool 12 and the first end 62 of the rod 60 being connected to the downwardly projecting actuator arm 48 of the lever 20. The rod 60 may be disposed through the body portion 26 of the base 18 such that movement of the lever 20 from the open to the closed position causes the first end 62 of the rod 60 to be displaced toward the proximal end 36 of the body portion 26 of the base 18, thereby moving the articulated member 16 of the tool 12.

The first end 62 of the actuator rod may be rounded, as shown in FIGS. 2–4, and the actuator arm 48 of the 1ever 20 may have a complementary-shaped opening therein to receive the round first end 62 of the actuator rod 60. The base 18 of the instrument 1 may define an opening 64 at the distal end 38 thereof complementary to the shape of the end of the body member 14 of the tool 12 such that the body portion 26 of the base 18 receives therein a portion of the body member 14 of the tool 12.

Referring now to FIGS. 3–6, the handle 10 of the instrument 1 may further comprise a means for securing the handle lever 20 at selected points throughout a range of motion of the handle lever 20 defined between and including the open position shown in FIG. 3 and the closed position shown in FIG. 4.

Figure 5:
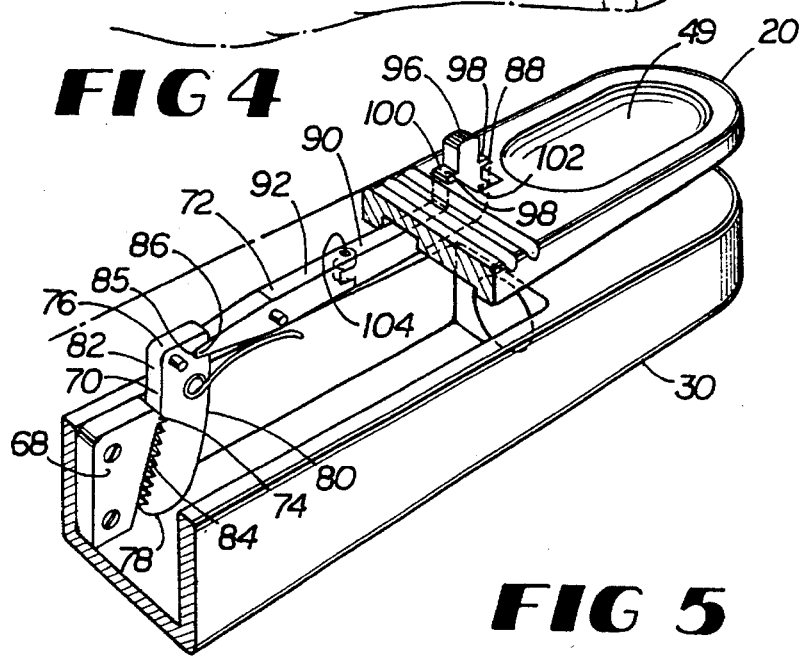
FIG. 5 is a perspective view of a fragmentary portion of an alternate embodiment of FIGS. 3 and 4.

In presently preferred embodiments shown in FIGS. 3–7, the securing means is a rachet 66, comprising: a pawl plate 68; a rachet arm 70; a rachet lever 72; and a means for urging the rachet arm 70 into an engaged with respect to the pawl 68 when the rachet lever 72 is in a rest position as shown in FIG. 5. The pawl plate 68 has a toothed surface 74 and is mounted on the base 18.

The rachet arm 70 has a top end 76 and a bottom end 78, a front surface 80 and a rear surface 82. The rear surface 82 of the rachet arm 70 has a plurality of rather teeth 84 complementary to the pawl tooth 74 of the pawl 68. The front surface 80 also has a notch 85 therein located adjacent the top end 76. The rachet arm 70 is pivotally mounted upon the handle lever 20 and projects downwardly such that the rear surface 82 of the rachet arm 70 is capable of engaging the toothed surface 74 of the pawl plate 68 throughout the range of motion of the handle lever 20.

The rachet lever 72 has a proximal end 86, a distal end 88, a top surface 90 and a central segment 92. The rachet lever 72 is pivotally mounted on the handle lever 20 such that the rachet lever 72 is moveable between a rest position (shown in FIG. 3), wherein the rachet arm 70 is in engagement with the pawl 68, and an operable position (shown in FIG. 4), wherein the rachet arm 70 is disengaged from the pawl 68.

The proximal end 86 of the ratchet lever 72 is complementary to and received within the notch 85 of the rachet arm 70 and moveable within the notch 85 between the rest and operable positions.

In the embodiments depicted in FIGS. 3–7, the handle lever 20 has an opening 94 through its first and second surfaces 40, 42 and the rachet lever 72 has an actuator tip 96 projecting upwardly from the distal end 88 of the rachet lever 72 such that the actuator tip 96 protrudes through the opening 94 in the handle lever 20.

In the embodiment shown in FIG. 5, the locking means comprises a shoulder 98 having a top surface 100 on the actuator tip 96 of the rachet lever 20 and a complementary locking shoulder slot 102 through the handle lever 20 adjacent to and in communication with the opening 94 in the handle lever 20. Depression and lateral movement of the actuator tip 96 of the rachet lever 72 into the shoulder slot 102 causes the top surface 100 of the shoulder 98 to contact the second surface 42 of the handle lever 20, thereby locking the rachet in the operable position (as shown in FIG. 4). To aid in lateral movement of the distal end 88 of the rachet lever 72, the rachet lever 72 may have an articulated joint 104 on the central segment 92.

Referring to FIG. 6 and FIG. 7, the locking means may alternatively comprise a pin 106 extending through the sides 45, 47 of the handle lever 20 perpendicular to the rachet lever 72 between the top surface 90 of the rachet lever 72 and the bottom surface 42 of the handle lever 20. The pin 106 has a notched portion 108 complementary in shape to the rachet lever 72. The pin 106 is moveable between a first position (shown in FIG. 7A) wherein the rachet lever 72 may be moveable into the notch 108 in the pin 106, thereby allowing movement of the rachet lever 72 between the rest position and the operable position and a second position (shown in FIG. 7B) wherein the pin 106 interferes with movement of the rachet lever 72, thereby locking the rachet lever 72 in the operable position.

It is contemplated by the present invention that the handle may be utilized on any suitable instrument with an articulated member on the tool including, but not limited to, conventional hand-held surgical instruments and minimally invasive surgical instruments (endoscopic instruments). The instruments of the present invention may be constructed from any suitable steel, aluminum and titanium. Examples of plastics include acetal, polycarbonate, ABS, and the like.

Although the present invention has been described with reference to specific details of certain embodiments thereof, it is not intended that such details should be regarded as limitations upon the scope of the invention except as and to the extent that they are included in the accompanying claims.

What is claimed is:

1. A hand-held surgical instrument comprising a handle and a tool with a body member having at least one articulated member thereon, the handle comprising:
   a) an elongated base having a body portion, a top surface, opposite bottom surface, a first side and an opposite second side, a proximal end and a distal end;
   b) an elongated lever having a first surface, an opposite second surface, a front end, a rear end and an actuator arm downwardly and non-pivotally projecting from said rear end;
   c) unitary means for connecting the rear end of said lever to the proximal end of said base and for normally biasing said lever in an open position, said unitary connecting and biasing means defining a horizontal pivot axis such that said lever pivots about said axis between an open position and a closed position, wherein said base and said lever are juxtaposed to each other along their length, with said lever extending forward from said unitary connecting and biasing means toward the distal end of said base, such that the second surface of said lever is adjacent to the top surface of said body portion and the actuator arm of said lever projects into the body portion of said base adjacent the proximal end thereof; and
   d) means for actuating the articulated member of said tool connected to the actuator arm of said lever, whereby movement of said lever from an open position to a closed position causes movement of the articulated member, wherein said actuating means comprises an actuator rod having a first end and a second end the second end of said rod being connected to the articulated member of said tool and the first end of said rod being connected to the downwardly and nonpivotally projecting actuator arm of said lever, wherein said rod is disposed through the body portion of said base such that movement of said lever form the open to the closed position causes the first end of said rod to be displaced toward the proximal end of the body portion of said base; thereby moving the articulated member of said tool.

2. The instrument of claim 1, wherein said base further comprises an arm upwardly projecting from the top surface of the proximal end, and said unitary connecting and biasing means connects to said arm.

3. The instrument of claim 2, wherein said unitary connecting and biasing means comprises a leaf spring having a preselected thickness with a first end and an opposite second end wherein the first end of said spring is connected to the first surface of said lever adjacent the proximal end thereof and the second end of said spring is connected to the upwardly projecting arm of said base.

4. The instrument of claim 1, wherein the first end of said actuator rod is round and the actuator arm of said lever defines a complementary-shaped opening therein to receive the round first end of said actuator rod.

5. The instrument of claim 1, wherein said base defines an opening at the distal end thereof complementary to the shape of the end of the body member of said tool such that the body portion of said base receives therein a portion of the body member of said tool.

6. The instrument of claim 1, further comprising a means for securing said handle lever at selected points throughout a range of motion of said handle lever defined between and including the open position and the closed position.

7. The instrument of claim 1, wherein said instrument is an endoscopic surgical instrument.

8. A hand-held surgical instrument comprising a handle and a tool with a body member having at least one articulated member thereon, the handle comprising;
   a) an elongated base having a body portion, a top surface, opposite bottom surface a first side and an opposite second side a proximal end and a distal end, and an arm upwardly projecting from the top surface of the proximal end;
   b) an elongated lever having a first surface, an opposite second surface, a front end, a rear end and an actuator arm downwardly projecting from said rear end;
   c) unitary means for connecting said arm on the rear end of said lever to the proximal end of said base and for normally biasing said lever in an open position, said unitary connecting and biasing means defining a pivot axis such that said lever horizontal pivots about said axis between an open position and a closed position, wherein said base and said lever are juxtaposed to each other along their length, with said lever extending forward from said unitary connecting and biasing means toward the distal end of said base, such that the second surface of said lever is adjacent to the top surface of said body portion and the actuator arm of said lever projects into the body portion of said base adjacent the proximal end thereof, wherein said unitary connecting and biasing means comprises a leaf spring having a preselected thickness with a first end and an opposite second end wherein the first end of said spring is connected to the first surface of said lever adjacent the proximal end thereof and the second end of said spring is connected to the upwardly projecting arm of said base, wherein said leaf spring is removably connected to said lever and said base such that said leaf spring may interchangeably be comprised of one of a plurality of leaf springs of different preselected thicknesses thereby varying the resistance of said biasing means; and d) means for actuating the articulated member of said tool connected to the actuating actuator arm of said lever, whereby movement of said lever from an open position to a closed position causes movement of the articulated member.

9. The instrument of claim 8, wherein said leaf spring is removably attached to said lever and said base by means of machine screws.

10. A hand-held surgical instrument comprising a handle and a tool with a body member having at least one articulated member thereon, the handle comprising:

a) an elongated base having a body portion, a top surface, opposite bottom surface, a first side and an opposite second side, a proximal end and a distal end;

b) an elongated lever having a first surface, an opposite second surface, a front end, a rear end and an actuator arm downwardly projecting from said rear end;

c) means for connecting the rear end of said lever to the proximal end of said base to allow said lever to pivot about a horizontal axis between an open position and a closed position, wherein said base and said lever are juxtaposed to each other along their length, with said lever extending forward from said connecting means toward the distal end of said base, such that the second surface of said lever is adjacent to the top surface of said body portion and the actuator arm of said lever projects into the body portion of said base adjacent the proximal end thereof;

d) means for normally biasing said lever in the open position;

e) means for actuating the articulated member of said tool connected to the actuator arm of said lever, whereby movement of said lever from an open position to a closed position causes movement of the articulated member; and f) means for securing said handle lever at selected points throughout a range of motion of said handle lever defined between and including the open position and the closed position, wherein said securing means is a rachet, said rachet comprising:

g) a pawl plate having a toothed surface thereon mounted on said base;

h) a rachet arm having a top end and a bottom end, a front surface and a rear surface, the rear surface having a plurality of rachet teeth complementary to the pawl tooth and the front surface having a notch therein located adjacent the top end, said rachet arm being pivotally mounted upon said handle lever, said rachet arm projecting downwardly such that the rear surface of said rachet arm is capable of engaging the toothed surface of said pawl plate throughout the range of motion of said handle lever;

i) a rachet lever having a proximal end, a distal end, a top surface and an intermediate and central segment, said rachet lever being pivotally mounted on said handle lever such that said rachet lever is moveable between a rest position, wherein said rachet arm is in engagement with said pawl, and an operable position, wherein said rachet arm is disengaged from said pawl, the proximal end of said ratchet lever being complementarily to and received within the notch of said rachet arm and moveable within the notch between the rest and operable positions;

j) means for urging said rachet arm into an engaged position with respect to said pawl when said rachet lever is in the rest position; and k) means for locking said rachet in the operable position.

11. The instrument of claim 10, wherein said handle lever has an opening through its first and second surfaces and said rachet lever has an actuator tip projecting upwardly from the distal end of said rachet lever such that the actuator tip protrudes through the opening in said handle lever.

12. The instrument of claim 10, wherein said locking means comprises:

a shoulder having a top surface on the actuator tip of said rachet lever; and b) a complementary locking shoulder slot through said handle lever adjacent to and in communication with the opening in said handle lever, such that depression and lateral movement of the actuator tip of said rachet lever into the shoulder slot causes the top surface of the shoulder to contact the second surface of said handle lever, thereby locking said rachet in the operable position.

13. The instrument of claim 10, wherein said rachet lever has an articulated joint on the central segment for allowing lateral movement of at least a portion of the distal end of said rachet lever.

14. The instrument of claim 10, wherein the locking means comprises: a pin extending through the sides of said handle lever perpendicular to said rachet lever between the top surface of said rachet lever and the bottom surface of said handle lever, said pin having a notched portion complementary in shape to said rachet lever, said pin being moveable between a first position wherein said rachet lever may be moveable into the notch in said pin, allowing movement of said rachet lever between the rest position and the operable position and a second position wherein said pin interferes with movement of said rachet lever, thereby locking said rachet lever in the operable position.

* * * * *